United States Patent [19]

Bezwada et al.

[11] Patent Number: 5,100,433
[45] Date of Patent: Mar. 31, 1992

[54] SUTURE COATED WITH A COPOLYMER COATING COMPOSITION

[75] Inventors: Rao S. Bezwada, Whitehouse Station; Alastair W. Hunter, Bridgewater; Shalaby W. Shalaby, Lebanon, all of N.J.

[73] Assignee: Ethicon, Inc., Somerville, N.J.

[21] Appl. No.: 613,323

[22] Filed: Nov. 8, 1990

[51] Int. Cl.$^5$ ............................................. A61B 17/00
[52] U.S. Cl. .................................. 606/230; 525/411; 528/354; 427/2
[58] Field of Search ................ 606/230, 231; 525/411, 525/415; 528/354, 359, 361; 427/2

[56] References Cited

U.S. PATENT DOCUMENTS

| | | | |
|---|---|---|---|
| 4,605,730 | 8/1986 | Shalaby et al. | 606/231 |
| 4,624,256 | 11/1986 | Messier et al. | 128/335.5 |
| 4,643,191 | 2/1987 | Bezwada et al. | 606/231 |
| 4,649,920 | 3/1987 | Rhum | 606/231 |
| 4,653,497 | 3/1987 | Bezwada et al. | 606/231 |
| 4,700,704 | 10/1987 | Jamiolkowski et al. | 606/231 |
| 4,791,929 | 12/1988 | Jarrett et al. | 128/335.5 |
| 4,857,602 | 8/1989 | Casey et al. | 606/231 |
| 4,983,180 | 1/1991 | Kawai et al. | 606/231 |
| 5,007,923 | 4/1991 | Bezwada et al. | 606/231 |

*Primary Examiner*—Stephen C. Pellegrino
*Assistant Examiner*—Gary Jackson
*Attorney, Agent, or Firm*—Matthew S. Goodwin

[57] ABSTRACT

A surgical suture having a coating thereon of a copolymer of a predominant amount of p-dioxanone and the balance ε-caprolactone, and a method for improving the knot tiedown performance of a suture by first coating a solution of the coating copolymer onto the surface of the suture and then removing the solvent from the coated suture.

13 Claims, No Drawings

SUTURE COATED WITH A COPOLYMER COATING COMPOSITION

BACKGROUND OF THE INVENTION

This invention relates to coated surgical sutures. More specifically, it relates to sutures coated with a coating copolymer and to a method for improving the knot tiedown performance of a surgical suture, especially an absorbable multifilament surgical suture.

Surgical sutures often require a surface coating to improve one or more of their performance properties. For example, a multifilament suture typically requires a surface coating to improve the tactile smoothness, pliability and tiedown performance of the suture, so it passes easily and smoothly through tissue during operative procedures. A monofilament suture may also require a surface coating to improve tiedown performance and to reduce tissue drag.

In response to the need for suitable coatings for surgical sutures, numerous patents have disclosed potential coating compositions. A polymer coating which has recently been developed shows significant promise as a suture coating is derived from a polymer solution of $\epsilon$-caprolactone in an appropriate organic solvent. The coating solution is typically applied to the surface of the suture using conventional techniques, and then the solvent is removed. Polycaprolactone is a biocompatable polymer with a relatively low melting point, a property which is essential for good coating characteristics. Additionally, sutures coated with polycaprolactone exhibit enhanced tiedown and handling characteristics. Unfortunately, polycaprolactone homopolymer is essentially nonabsorbable because it retains some of its mass and mechanical integrity in vivo for periods up to one year, which is too long for numerous surgical applications.

In an effort to improve the bioabsorbability and other properties of a polycaprolactone coating polymer, the polymer composition has been modified by incorporating copolymerizable monomers or lubricating agents therein. For example, U.S. Pat. No. 4,624,256 discloses a suture coating copolymer of at least 90 percent $\epsilon$-caprolactone and a biodegradable monomer, and optionally a lubricating agent. Examples of monomers for biodegradable polymers disclosed include glycolic acid and glycolide, as well as other well known monomers typically used to prepare polymer fibers or coatings for multifilament sutures. U.S. Pat. No. 4,791,929 discloses a bioabsorbable coating of a copolymer of at least 50 percent $\epsilon$-caprolactone and glycolide. Sutures coated with such copolymers are reported to be less stiff than sutures coated with other materials, and the physical properties of the coated suture are also reported to be acceptable.

Unfortunately, the problem of adequate bioabsorbability of homopolymers and copolymers of $\epsilon$-caprolactone for suture coating applications still remains. One of the difficulties a skilled polymer chemist has faced in solving this problem is in developing a faster absorbing polymer containing $\epsilon$-caprolactone without sacrificing the tiedown performance or physical properties of multifilament sutures coated with such a polymer. In view of the deficiencies with the known art polycaprolactone coatings, it would be most desirable to accomplish this goal.

SUMMARY OF THE INVENTION

In one aspect, the invention is a suture having its surface coated with a coating copolymer of a predominant amount of p-dioxanone and the balance $\epsilon$-caprolactone. The amount of copolymer coated on the surface of the suture is an amount effective to improve its knot tiedown performance relative to the knot tiedown performance of the uncoated suture.

In another aspect, the invention is a method of improving the knot tiedown performance of a suture. This method comprises the steps of coating the surface of the suture with an effective amount of a solution of the coating copolymer described above in an organic solvent and then removing the solvent from the coated suture.

The copolymer coating of this invention can be applied to the surface of a suture using conventional techniques. The knot tiedown performance of the coated suture, which is an indication of its tactile smoothness, dramatically improves without sacrificing the tensile properties of the coated suture. Surprisingly, these improvements in properties are achieved while increasing the rate of absorption of the coating copolymers relative to the absorption rate of prior art copolymers containing $\epsilon$-caprolactone.

DETAILED DESCRIPTION OF THE INVENTION

A predominant amount of p-dioxanone (PDO) generally refers to an amount of PDO greater than 50 mole percent of the comonomer composition from which the copolymer of this invention is derived. PDO is the predominant component of the copolymer because of its ability to enhance the physical properties of coated multifilament sutures and to increase the absorption rate of the coating copolymer. Preferably, the amount of PDO used ranges from about 55 to about 95, more preferably from about 55 to about 80 mole percent. The most preferred amount of PDO used ranges from about 55 to about 70 mole percent.

The amount of copolymer coated onto the surface of the suture to improve knot tiedown performance will generally depend on the intrinsic viscosity of the copolymer, which is a function of its molecular weight, and can readily be determined empirically. In most instances, the required amount of copolymer coating decreases as its intrinsic viscosity increases. Advantageously, the amount of the copolymer coated onto the suture ranges from about 0.1 to about 20, preferably from about 1 to about 12 percent of the weight of the coated suture. Generally, amounts greater than 20 weight percent may significantly compromise the knot security of the coated suture and amounts below 0.1 weight percent may fail to achieve any appreciable improvement in suture properties.

The copolymer coatings of this invention are typically characterized by an intrinsic viscosity as determined in a 0.1 g/dl solution of hexafluoroisopropanol (HFIP) at 25° C. ranging from about 0.1 to about 1.5, preferably from about 0.2 to about 0.8. A coating copolymer with an intrinsic viscosity below 0.1 may fail to significantly improve the knot tiedown of a coated suture, and a coating copolymer with an intrinsic viscosity above 1.5 may increase the stiffness of the coated suture.

Sutures within the scope of this invention can be of any type used or contemplated for operative procedures. The suture can be synthetic or natural, absorbable or nonabsorbable, or a monofilament or multifilament in a braided, twisted or covered form. In addition, the sutures can be attached to one or more needles, if desired. Examples of absorbable monofilament sutures include natural sutures such as surgical gut and collagen, and synthetic sutures such as homopolymers and copolymers of p-dioxanone. Examples of absorbable multifilament sutures include sutures prepared from fiber-forming polymers of one or more lactones, e.g. Vicryl® poly(lactide-co-glycolide) multifilament suture. Examples of nonabsorbable monofilament and multifilament sutures include nylon, polypropylene, steel, polyvinylidene fluoride, linen, cotton, silk, and polyesters such as polyethylene terephthalate (PET). The preferred sutures are absorbable, multifilament sutures The most preferred suture is Vicryl® poly(lactide-co-glycolide) multifilament suture.

The organic solvent for the coating copolymer of this invention is advantageously a solvent which has a normal boiling Point no greater than 120° C. Examples of suitable organic solvents include but are not limited to chloroform, methylene chloride, 1,1,2-trichloroethane, and trifluoroethanol.

The coating can easily be prepared by simply dissolving the copolymer into the appropriate organic solvent. The concentration of the copolymer in solution will, of course, depend on the amount of copolymer desirably coated onto the surface of the suture, but generally should range from about 1 to about 25, preferably from about 2 to about 18 weight percent.

Once a solution of the coating copolymer is prepared, a suture can be coated using conventional coating techniques, e.g. dipping, spraying, etc. After the coating is applied, the solvent can be removed by drying in air, or by other techniques well known in the art, for example, removing the solvent at an elevated temperature under vacuum.

The organic solvent and the preparation of a coating solution for application is normally required for coating multifilament sutures. However, an alternative approach is feasible for coating monofilament sutures without requiring the preparation of coating solution. If a synthetic monofilament suture is to be coated, then the fiber-forming polymer from which the suture is derived could be coextruded with a suitably low molecular weight coating copolymer so that the copolymer could exude to the surface of the fiber during extrusion to increase its tactile smoothness. Such methods have been demonstrated to enhance the lubricity and knotting characteristics of the fiber-forming polymer.

The following examples illustrate but are not intended to limit the scope of the claimed invention. In the examples, the tensile properties, tiedown roughness and knot security are each determined using an Instron Tensile Tester. The tensile properties, i.e. the straight and knot tensile strength and the percent elongation, are determined generally according to the procedures described in U.S. Pat. No. 4,838,267. The tiedown roughness is a measure of the knot tiedown performance. It provides an indication of the force required to slide a knot down a suture, and it is determined generally according to the procedure described in U.S. Pat. No. 3,942,532. The knot security, which provides an indication as to the number of throws required to secure a knot so that it fails to slip before cleanly breaking, is measured by first tieing a conventional square knot around a mandrel, pulling the knot apart on the Instron Tester to observe whether slipping occurs, and if so, then tieing knots with additional throws until 20 out of 20 knots break cleanly without slipping.

EXAMPLE 1

Coating Copolymer of PDO/$\epsilon$-Caprolactone at 65/35 By Mole Initial Composition A flame dried, 250 ml, round bottom single neck flask is charged with 66.36 g (0.65 mole) of p-dioxanone, 35.95 g (0.35 mole) of $\epsilon$-caprolactone, 0.73 milliliter of propylene glycol (USP grade), and 0.12 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for 24 hours, lowered to 110° C. and maintained there for about 24 hours. The copolymer is dried for about 80 hours at 80° C. under high vacuum (0.1 mm Hg) to remove any unreacted monomer. The copolymer has an intrinsic viscosity (I.V.) of 0.49 dl/g in HFIP at 25° C. The mole ratio of PCL/PDS/PDO is found to be 40.4/54.8/4.8 by NMR (PCL and PDS refer to polymerized moieties of c-caprolactone and p-dioxanone, respectively). The copolymer is tested for absorption and the data is reported in Table 1.

EXAMPLE 2

Copolymer of PDO/e-caprolactone at 70/30 By Mole Initial Composition

The procedure of Example 1 is substantially repeated, except that the reaction flask is charged with 71.46 g (0.7 mole) of p-dioxanone, 34.24 g (0.3 mole) of $\epsilon$-caprolactone, 0.73 ml of propylene glycol USP, and 0.12 ml of stannous octoate (0.33 molar in toluene). The copolymer has an I.V. of 0.46 dl/g in HFIP at 25° C. The mole ratio of PCL/PDS/PDO is found to be 36.0/59.3/4.7 by NMR.

EXAMPLE 3

Copolymer of PDO/c-caprolactone at 80/20 By Mole Initial Composition

The procedure of Example 1 is substantially repeated, except that the reaction flask is charged with 81.67 g (0.8 mole) of p-dioxanone, 22.83 g (0.2 mole) of $\epsilon$-caprolactone, 0.73 ml of propylene glycol USP, and 0.12 ml of stannous octoate (0.33 molar in toluene). The copolymer has an I.V. of 0.41 dl/g in HFIP at 25° C. The mole ratio of PCL/PDS/PDO is found to be 25.0/71.1/3.9 by NMR. The copolymer is tested for absorption and data is reported in Table 1.

COMPARATIVE EXAMPLES

EXAMPLE 4

Coploymer of PDO/Caprolactone at 20/80 By Mole Initial Composition

The procedure of Example 1 is substantially repeated, except that the reaction flask is charged with 91.31 g (0.8 mole) of $\epsilon$-caprolactone, 20.42 g (0.2 mole) of p-dioxanone, 0.73 milliliters of propyleneglycol-USP, and 0.12 milliliters of stannous octoate (0.33 molar in toluene). The copolymer is isolated and dried under vacuum to remove any unreacted monomers. A weight loss of 6.3% is observed. The copolymer has an I.V. of 0.56 dl/g in HFIP at 25° C. The mole ratio of PCL/PDS/PDO is found to be 70.8/26.8/2.4 by NMR.

The copolymer is tested for absorption and the data is reported in Table 1.

EXAMPLE 5

Copolymer of PDO/Caprolactone at 35/65 By Mole Initial Composition

The procedure of Example 1 is substantially repeated, except that the reaction flask is charged with 74.19 g (0.65 mole) of ε-caprolactone, 35.73 g (0.35 mole) of p-dioxanone, 0.73 ml of propylene glycol USP, and 0.12 ml of stannous octoate (0.33 molar in toluene). The copolymer was isolated and dried under vacuum to remove any unreacted monomers. The copolymer has an I.V. of 0.56 dl/g in HFIP at 25° C. The mole ratio of PCL/PDS/PDO is found to be 67.3/30.5/2.2 by NMR. The copolymer is tested for absorption and the data is reported in Table 1.

TABLE 1

CHARACTERIZATION AND ABSORPTION OF COATING COPOLYMERS

| Characterization | Example No. | | Comparative Examples | |
|---|---|---|---|---|
| | 1 | 3 | 4 | 5 |
| Mole ratio of PDO/Caprolactone | 65/35 | 80/20 | 20/80 | 35/65 |
| Absorption | | | | |
| In vitro hydrolysis at 100° C. (sterile water) | | | | |
| Percent nonhydrolyzed copolymer[1] at | | | | |
| 2 days | 6.07 | 5.96 | 88.72 | 13.78 |
| 2 days (repeat) | 7.46 | 0.39 | 86.99 | 39.45 |
| In vitro hydrolysis at 50° C. (buffer pH 7.27) | | | | |
| Percent nonhydrolyzed copolymer[1] at | | | | |
| 98 days | 15.36 | 4.79 | 86.16 | 44.85 |
| 112 days | 11.68 | 3.26 | 86.64 | 36.75 |

[1]Determined by measuring weight loss of copolymer after the indicated number of days.

The data from Table 1 shows a significant increase in the rate of hydrolysis for the copolymers of this invention compared to prior art copolymers containing ε-caprolactone. The rate of hydrolysis is a measure of the rate of absorption since synthetic copolymers degrade via hydrolysis.

A 5 weight percent coating solution of each of the copolymers of Examples 1-3 in trifluoroethanol is prepared. A size 2/0 (USP standard) Vicryl ® poly(lactide-co-glycolide) braided multifilament suture is coated at room temperature with each coating solution using conventional laboratory coating equipment, and the coated suture is subsequently dried in air at an elevated temperature to remove the solvent. The tensile and tiedown roughness properties of the coated sutures are reported in Table 2 as Examples 6-8, which correspond to Example 1-3, respectively, and compared to the tensile and tiedown properties of an uncoated Vicryl ® poly(lactide-co-glycolide) braided multifilament suture.

TABLE 2

PROPERTIES OF VICRYL ® POLY(LACTIDE-CO-GLYCOLIDE) SUTURE COATED WITH COATING COPOLYMER OF PDO/ε-CAPROLACTONE

| | EXAMPLE NO. | | | |
|---|---|---|---|---|
| | 6 | 7 | 8 | Uncoated |
| | 65/35 by mole PDO/ε-caprolactone | 70/30 by mole PDO/ε-caprolactone | 80/20 by mole PDO/ε-caprolactone | Suture Control — |
| Percent Solids[1], wt. | 2.6 | 2.4 | 2.5 | — |
| Suture Diameter, mils. | 12.8 | 13.0 | 12.9 | 13.6 |
| Dry Tiedown Roughness, gms. | 163.8 | 133.1 | 124.8 | 442 |
| Wet Tiedown Roughness[2], gms. | 150.5 | 155.5 | 218.7 | 509 |
| Wet Knot Security | 4 | 4 | 3 | 2 |
| Dry Knot Tensile Strength, kpsi | 8.9 | 9.4 | 9.3 | 8.7 |
| Wet Knot Tensile Strength, kpsi | 73.9 | 71.4 | 71.6 | 62.2 |
| Dry Straight Tensile Strength, kpsi | 110.9 | 112.2 | 111.0 | 108.4 |
| Percent Elongation | 17.0 | 17.5 | 17.7 | 17.9 |

[1]Determined by measuring the difference in weight between the coated and uncoated suture.
[2]Wet properties are determined after soaking the suture in water at 25° C. for at least 24 hours.

The results indicate that the Vicryl ® poly(lactide-co-glycolide) suture coated with varying compositions of a copolymer of PDO and ε-Caprolactone exhibits significantly improved dry and wet tiedown roughness relative to that of the uncoated suture. The improved roughness is achieved without sacrificing knot security or the tensile properties of the uncoated suture. Generally, a wet tiedown roughness of less than 225 grams, preferably less than 200 grams, for the coated sutures of this invention can be readily obtained.

Similar outstanding results can be obtained with other copolymer coatings within the scope of the claimed invention.

In the claims:

1. A suture wherein the surface thereof is coated with a coating copolymer of a predominant amount of p-dioxanone and the balance ε-caprolactone, in an amount effective to improve the knot tiedown performance of the coated suture relative to the knot tiedown performance of the uncoated suture.

2. The suture of claim 1 wherein the amount of p-dioxanone in the coating copolymer is between about 55 and about 95 mole percent.

3. The suture of claim 2 wherein the amount of p-dioxanone in the coating copolymer is between about 55 to about 80 mole percent.

4. The suture of claim 3 wherein the amount of copolymer coated onto the surface of the suture ranges between about 1 to about 12 percent of the weight of the coated suture.

5. The suture of claim 4 wherein the intrinsic viscosity of the coating copolymer is between about 0.2 dl/g and about 0.8 dl/g.

6. The suture of claim 5 wherein the suture is a multifilament suture.

7. The suture of claim 7 wherein the multifilament suture is an absorbable suture.

8. The suture of claim 7 wherein the suture is prepared from a fiber-forming polymer of one or more lactones.

9. The suture of claim 8 wherein the suture is Vicryl® poly(lactone-co-glycolide) braided multifilament suture.

10. A method of improving the knot tiedown performance of a suture comprising the steps of:
   a) coating the surface of the suture with an effective amount of a solution of a copolymer of a predominant amount of p-dioxanone and the balance ε-caprolactone in an organic solvent, and then
   b) removing the solvent from the coated suture.

11. The method of claim 10 wherein the solution of coating copolymer is a solution of between about 1 and about 25 weight percent of the copolymer in trifluoroethanol, chloroform, methylenechloride or 1,1,2-trichloroethane.

12. The method of claim 11 wherein the solvent is removed by drying the coated suture in air.

13. The method of claim 12 wherein the coated suture is dried at an elevated temperature.

* * * * *